United States Patent
Mehta et al.

(10) Patent No.: US 8,563,535 B2
(45) Date of Patent: Oct. 22, 2013

(54) COMBINATION COMPOSITION COMPRISING BENZOYL PEROXIDE AND ADAPALENE

(76) Inventors: Kamal Mehta, Bhilwara (IN); Lalatendu Panigrahi, Bhubaneswar (IN); Uday Kumar Nayak, Navi Mumba (IN); Balakrishna Patro, Ganjam (IN)

(*) Notice: Subject to any disclaimer, the term of this patent is extended or adjusted under 35 U.S.C. 154(b) by 0 days.

(21) Appl. No.: 13/429,314

(22) Filed: Mar. 23, 2012

(65) Prior Publication Data

US 2012/0252897 A1  Oct. 4, 2012

(30) Foreign Application Priority Data

Mar. 29, 2011 (IN) ............ 963/MUM/2011

(51) Int. Cl.
*A61K 31/60* (2006.01)

(52) U.S. Cl.
USPC ............. 514/165; 514/544; 514/24; 514/559; 514/714

(58) Field of Classification Search
USPC ............ 514/165, 544, 24, 559, 714
See application file for complete search history.

(56) References Cited

U.S. PATENT DOCUMENTS

| | | | |
|---|---|---|---|
| 4,189,501 A | | 2/1980 | Fulton, Jr. |
| 5,932,228 A | * | 8/1999 | Hall et al. ............ 424/401 |
| 6,117,843 A | * | 9/2000 | Baroody et al. ............ 514/24 |
| 7,820,186 B2 | | 10/2010 | Orsoni et al. |
| 7,964,202 B2 | | 6/2011 | Orsoni et al. |
| 2003/0064959 A1 | * | 4/2003 | Sawada et al. ........... 514/54 |
| 2007/0248555 A1 | * | 10/2007 | Watson ............ 424/70.13 |
| 2008/0033047 A1 | * | 2/2008 | Chacra Vernet et al. ...... 514/569 |
| 2009/0253788 A1 | | 10/2009 | Vernet et al. |
| 2010/0166852 A1 | | 7/2010 | Mallard et al. |

FOREIGN PATENT DOCUMENTS

| | | |
|---|---|---|
| WO | 03055472 A1 | 7/2003 |
| WO | 2009092954 A1 | 7/2009 |

OTHER PUBLICATIONS

Bollinger, Journal of Pharmaceutical Science, 1977, vol. 66, No. 5, p. 718-722.

B. Martin et al., Br. J. Dermatol. (1998) 139, (suppl. 52), 8-11).

* cited by examiner

*Primary Examiner* — Ali Soroush

(74) *Attorney, Agent, or Firm* — M. Carmen & Associates, PLLC

(57) ABSTRACT

An aqueous gel composition of the present invention comprising about 0.1 to 0.3 wt % adapalene and about 2.5 to 5.0 wt % benzoyl peroxide, as active ingredients, wherein both the active ingredients are stabilized in hydrophilic gelling matrix of pH dependent gelling agent comprising crosslinked, acrylic acid-based polymer(s).

4 Claims, No Drawings

COMBINATION COMPOSITION COMPRISING BENZOYL PEROXIDE AND ADAPALENE

PRIORITY

This application claims priority under 35 U.S.C. 119 (a)-(e) to Indian Provisional Application No. 963/MUM/2011, filed on Mar. 29, 2011, the contents of which is hereby incorporated by reference.

BACKGROUND OF THE INVENTION

1. Technical Field

The present invention generally relates to a stable topical pharmaceutical composition for the treatment of Acne vulgaris comprising adapalene or a pharmaceutically acceptable salt thereof and benzoyl peroxide and a process for preparing the same.

2. Description of the Related Art

Acne vulgaris is an inflammatory disease of the sebaceous glands characterized by an eruption of the skin, often pustular in nature but not supportive. Acne is a common affliction of the adolescent and affects a small but significant percentage of the adult population. Acne involvement results in unsightly lesions, particularly on the face, and in some cases results in severe scarring.

There are a variety of methods of administering various agents for treating Acne vulgaris, including either orally or topically to the skin. Nevertheless, Acne vulgaris is seldom cured and only can be controlled with difficulty. In no case has a treatment designed for any of the aforementioned causes proven to be uniformly effective. The market is replete with products that contain single component topical skin ointments, where such components may contain, inter alia, benzoyl peroxide or adapalene.

Of the more typical ingredients in topical treatments are benzoyl peroxide (BPO) and adapalene, which are known to be effective in treating mild to moderate cases of non-inflammatory acne. Benzoyl peroxide acts by destroying Pseudomonas acnes, the bacteria that causes the condition acne. Benzoyl peroxide acts as an antiseptic and as an oxidizing agent, reducing the number of comedones, or blocked pores. While, adapalene, otherwise known as 6-[3-(1-adamantyl)-4-methoxyphenyl]-2-naphthoic acid, is purported to bind to specific retinoic acid nuclear receptors but not to the cytosolic receptor protein. Although the exact mode of action of adapalene is unknown, it had been suggested that topical adapalene may normalize the differentiation of follicular epithelial cells resulting in decreased microcomedone formation. Ideally, a combination drug should have both comedogenesis and bacteriostatic effect in acne treatment. However, an obstacle to a combination utilizing adapalene is the instability of adapalene in the presence of BPO.

The market also offers dual component anti-acne compositions. Some of which are as described. Commercial composition EPIDUO® comprises adapalene 0.1%; and benzoyl peroxide 2.5% in the form of aqueous gel with inactive ingredients acrylamide/sodium acryloyldimethyltaurate copolymer, docusate sodium, edetate disodium, glycerin, isohexadecane, POLOXAMER™124, polysorbate 80, propylene glycol, purified water, and sorbitan oleate.

U.S. Pat. No. 7,820,186 describes aqueous gel composition for once-daily treatment of common acne comprising anti-acne actives consisting of 0.1% adapalene and/or at least one pharmaceutically acceptable salt thereof, 2.5% dispersed benzoyl peroxide, and further comprising 4% acrylamide sodium acryloyldimethyltaurate copolymer/isohexadecane/polysorbate 80 gelling agent. The gelling agent described is a pH independent gelling agent.

WO PCT International Publication No. 2009092954 describes composition comprising, at least one retinoid and dispersed benzoyl peroxide and at least one gelling agent from carrageenan family.

U.S. Pre-grant Publication No. US2010/0166852 describes a cream gel dermatological composition useful for the prevention or treatment of dermatological conditions, comprising a homogeneous dispersion of a fatty phase in an aqueous phase, including at least one dispersed retinoid and dispersed benzoyl peroxide, at least one lipophilic compound and at least one gelling agent.

U.S. Pre-grant Publication No. 2009/0253788 directed to a treatment regimen for reducing the number of acne lesions, comprising administering a combination composition which comprises adapalene or a pharmaceutically acceptable salt thereof and benzoyl peroxide.

The pH independent gelling polymers described in the prior art are expensive. The present invention presents a cost-effective stable composition of adapalene and benzoyl peroxide with easily procured pH dependent gelling polymers; and the process of preparation can be upscaled for commercial usage.

SUMMARY OF THE INVENTION

The present invention relates to a topical pharmaceutical composition for the treatment of Acne vulgaris comprising adapalene or a pharmaceutically acceptable salt thereof and benzoyl peroxide, as active ingredients; and a pH dependent gelling agent; wherein both the active ingredients are stabilized in hydrophilic gelling matrix of pH dependent gelling agent.

The topical composition of the present invention is an aqueous gel comprising adapalene and benzoyl peroxide and a pH dependent gelling agent; wherein both the active ingredients are stabilized in hydrophilic gelling matrix of pH dependent gelling agent.

The aqueous gel composition comprising adapalene and benzoyl peroxide and a pH dependent gelling agent selected from the group of crosslinked, acrylic acid-based polymer(s); wherein both the active ingredients are stabilized in hydrophilic gelling matrix of pH dependent gelling agent.

The aqueous gel composition comprising 0.1 wt % adapalene and 2.5% wt % benzoyl peroxide and 0.1 to 10 wt % carbomer(s) as a pH dependent gelling agent; wherein both the active ingredients are stabilized in hydrophilic gelling matrix of pH dependent gelling agent.

The aqueous gel composition comprising 0.1 wt % adapalene and 2.5% wt % benzoyl peroxide and 0.1 to 10 wt % carbomer(s) as a pH dependent gelling agent and 0.1 to 10 wt % penetration enhancer; wherein both the active ingredients are stabilized in hydrophilic gelling matrix of pH dependent gelling agent.

DETAILED DESCRIPTION OF THE INVENTION

An aqueous gel composition of the present invention comprises adapalene or a pharmaceutically acceptable salt thereof and benzoyl peroxide wherein both the active ingredients are stabilized in hydrophilic gelling matrix of pH dependent gelling agent comprising crosslinked, acrylic acid-based polymer(s).

Adapalene (6-[3-(1-adamantyl)-4-methoxyphenyl]-2-naphthoic acid) is a naphthoic acid derivative with retinoid and anti-inflammatory properties. This molecule was developed for the topical treatment of common acne and of dermatoses sensitive to retinoids.

The term "adapalene or a pharmaceutically acceptable salt thereof" means the salts formed with a pharmaceutically acceptable base, especially mineral bases such as sodium hydroxide, potassium hydroxide and ammonia or organic bases such as lysine, arginine or N-methylglucamine.

The expression "adapalene or a pharmaceutically acceptable salt thereof in combination of benzoyl peroxide" means a single composition comprising both adapalene or salts thereof and benzoyl peroxide.

A single gel composition comprising about 0.01 to 1.0 wt %, preferably about 0.1 to 0.3 wt % of adapalene or salts thereof and about 1.0 to 10.0 wt %, preferably 2.0 to 6.0 wt % of benzoyl peroxide.

The present invention provides an aqueous gel composition comprising adapalene and benzoyl peroxide, as active ingredients, wherein both the active ingredients are stabilized in a hydrophilic gelling matrix of pH dependent gelling agent, comprising crosslinked, acrylic acid-based polymer(s) and a penetration enhancer. Herein the phrase "stabilized in hydrophilic gelling matrix of pH dependent gelling agent" is intended to mean that the gel of the present invention meets the requirements prescribed for benzoyl peroxide gel in USP30-NF25 (U.S. Pharmacopoeia) in terms of purity.

The present invention provides an aqueous gel composition comprising about 0.1 to 0.3 wt % adapalene and about 2.5 to 5.0 wt % benzoyl peroxide and about 0.1 to 10 wt % crosslinked, acrylic acid-based polymer(s) and about 0.1 to 10 wt % penetration enhancer; wherein both the active ingredients are stabilized in hydrophilic gelling matrix of pH dependent gelling agent.

The present invention provides an aqueous gel composition comprising 0.1 wt % adapalene and 2.5% wt benzoyl peroxide and 0.1 to 10 wt %, preferably 0.5 to 5 wt % crosslinked, acrylic acid-based polymer(s) and 0.1 to 10 wt %, preferably 0.5 to 5 wt % penetration enhancer and 0.05 to 5 wt %, preferably 0.2 to 1.5 wt % surfactant and about 5 to 90 wt % solvent; wherein both the active ingredients are stabilized in hydrophilic gelling matrix of pH dependent gelling agent.

The present invention provides a pharmaceutical composition comprising optionally a stabilizer, whereby the stabilizer helps to minimize the degradation of benzoyl peroxide to benzoic acid. The most preferred stabilizer includes Silicon Dioxide (RxCIPIENTS®GL200 and RxCIPIENTS®GL100 Supplied by Huber Engineered Materials).

The present invention provides pharmaceutical compositions comprising other ingredients that are also typically used in pharmaceutical compositions such as, for example, chelating agent like disodium ethylenediaminetetraacetic acid (EDTA), and humectants like glycerin or sorbitol.

The present invention provides pharmaceutical compositions comprising a neutralizer for the adjustment of pH as the degree of polymerization is pH dependent. Useful neutralizers include, but are not limited to, an alkali metal hydroxide such as, for example, sodium hydroxide, potassium hydroxide, ammonium hydroxide and the like and mixtures thereof. Preferably the neutralizer is sodium hydroxide.

Useful solvents include, but are not limited to, propylene glycol and purified water or combination of thereof, which is chemically stable and does not support the growth of microorganisms. Topical preparation prepared from this solvent does not dry up on the skin.

The gel forming agent also works by the principle of copolymerization. Under alkaline pH, carbomer in the presence of water undergoes cross linking and forms a gel like structure. The degree of polymerization is dependent upon the pH. At a threshold pH, the viscosity achieved by the polymer grade is the maximum.

The pH dependent gelling agents of present invention (degree of polymerization is pH dependent) are crosslinked, acrylic acid-based polymer(s) commonly known as the polymers of "carbomer family". Particularly the pH dependent gelling agent is one or more polymers selected from the group comprising CARBOPOL® homopolymers or copolymers. These homopolymers are the polymers of acrylic acid crosslinked with allyl sucrose or allylpentaerythritol, and are commercially available as CARBOPOL®940, CARBOPOL® 980. While CARBOPOL® copolymers are the polymers of acrylic acid, modified by long chain (C10-C30) alkyl acrylates, and crosslinked with allylpentaerythritol such as PEMULEN™TR-1 NF and PEMULEN™TR-2 NF polymers. On the other hand, CARBOPOL® interpolymers are carbomer homopolymers or copolymers that contain a block copolymer of polyethylene glycol and a long chain alkyl acid ester, such as CARBOPOL® Ultrez10 NF Polymer, CARBOPOL®ETD 2020 NF Polymer.

In another aspect, the present invention provides the pH dependent gelling agent comprising NOVEON® polycarbophil, which is a polymer of acrylic acid crosslinked with divinyl glycol, such as for example, NOVEON® AA-1 USP Polycarbophil.

In yet another aspect, the present invention provides pH dependent gelling agent to be sodium alginate and sodium carboxymethylcellulose.

In order to prepare a uniform gel, dispersing agents such as alcohol or glycerin can be added, or the gelling agent can be dispersed by trituration, mechanical mixing or stirring, or combinations thereof.

The present invention provides penetration enhancers, selected from the group comprising of isohexadecane, isopropyl myristate, octyldodecanol, oleyl alcohol, medium chain triglyceride, cyclomethicone, ethoxydiglycol diusopropyl adipate, dimethyl isosorbide, 1,2,6-hexanetriol, and benzyl alcohol or mixtures thereof. Preferably, isohexadecane or octyldodecanol or cyclomethicone in the range of about 0.5 to 2 wt %.

In one aspect, the present invention provides surfactants to stabilize drug dispersion of ingredients, wherein the surfactant comprises a nonionic, anionic, cationic or amphoteric surfactant. Suitable emulsifiers include, but are not limited to, polyoxyethylenated and/or polyoxypropylenated copolymers (such as POLOXAMER™ family and more particularly POLOXAMER™124 and/or POLOXAMER™182), glyceryl stearate, polyethylene glycol 100 stearate, glyceryl monostearate, polysorbate 80, sorbitan monostearate, sorbitan oleate, polyglyceryl-4 oleate, sodium docusate, polyoxyethylene(4) lauryl ether and sodium lauryl sulphate and mixtures thereof. Preferably, POLOXAMER™124.

In one aspect, the present invention includes only one surfactant.

In one aspect, the present invention provides a composition comprising 0.1% adapalene, 2.5% benzoyl peroxide, 0.1% disodium EDTA, 4.0% glycerin, 4.0% propylene glycol, 0.05% sodium docusate, 0.2% POLOXAMER™124, 1.1% CARBOPOL® 980, 0.5% sorbitan oleate and 1% isohexadecane in purified water; wherein both the active ingredients are stabilized in hydrophilic gelling matrix of pH dependent gelling agent. The pH of the bulk is adjusted with 10% sodium hydroxide solution to pH 4.6.

In another aspect, the present invention provides a composition comprising 0.1% adapalene, 2.5% benzoyl peroxide, 0.1% disodium EDTA, 4.0% glycerin, 4.0% propylene glycol, 0.05% sodium docusate, 0.2% POLOXAMER™124, 1.1% CARBOPOL®980 and 1% octyldodecanol in purified water; wherein both the active ingredients are stabilized in hydrophilic gelling matrix of pH dependent gelling agent. The pH of the bulk is adjusted with 10% sodium hydroxide solution to pH 4.6.

In yet another aspect, the present invention provides a composition comprising 0.1% adapalene, 2.5% benzoyl peroxide, 0.1% disodium EDTA, 4.0% glycerin, 4.0% propylene glycol, 0.05% sodium docusate, 0.2% POLOXAMER™124, 1.1% CARBOPOL® 980, 0.5% sorbitan oleate and 1% cyclomethicone in purified water; wherein both the active ingredients are stabilized in hydrophilic gelling matrix of pH dependent gelling agent. The pH of the bulk is adjusted with 10% sodium hydroxide solution to pH 4.6.

In another aspect, the present invention provides a composition comprising 0.1% adapalene, 2.5% benzoyl peroxide, 0.1% disodium EDTA, 5.0% glycerin, 10.0% propylene glycol, 0.3% sodium docusate, 0.2% POLOXAMER™124, 0.7% CARBOPOL®980, 0.3% PEMULEN™ TR-1, 1.0% sorbitan oleate and 1.0% cyclomethicone in purified water; wherein both the active ingredients are stabilized in hydrophilic gelling matrix of pH dependent gelling agent. The pH of the bulk is adjusted with 10% sodium hydroxide solution to pH 4.6.

In one more aspect, the present invention provides a process for the preparation of stable aqueous gel composition comprising a) preparing gelling phase comprising acrylic acid polymers in purified water b) preparing adapalene drug dispersion in purified water comprising surfactant and humectants c) preparing benzoyl peroxide drug dispersion in propylene glycol d) adding (b) and (c) into (a) with homogenization and then e) adding penetrating agent with homogenization; finally (f) adjust the pH with f) 10% sodium hydroxide solution; wherein both the active ingredients are stabilized in hydrophilic gelling matrix of pH dependent gelling agent.

The following examples are provided to enable one skilled in the art to practice the invention and are merely illustrative of the invention. The examples should not be read as limiting the scope of the invention as defined in the claims.

EXAMPLES

Example 1

Preparation of an Aqueous Gel Composition Comprising CARBOPOL®980 as Gelling Agent and Isopropyl Myristate as Penetrating Agent The ingredients for use in this example are set forth below in Table 1.

TABLE 1

| Sr. No. | Ingredients/Components | Qty. in % w/w |
|---|---|---|
| 1 | Adapalene | 0.1 |
| 2 | Benzoyl peroxide | 2.5 |
| 3 | Disodium EDTA | 0.1 |
| 4 | Glycerin | 4.0 |
| 5 | Propylene Glycol | 4.0 |
| 6 | Sodium docusate | 0.05 |
| 7 | POLOXAMER ™-124 | 0.2 |
| 8 | CARBOPOL ® 980 | 1.1 |
| 9 | Sorbitan oleate | 0.5 |
| 10 | Isopropyl myristate | 1.0 |

TABLE 1-continued

| Sr. No. | Ingredients/Components | Qty. in % w/w |
|---|---|---|
| 11 | Sodium hydroxide | 0.2 |
| 12 | Purified water | 86.25 |

Manufacturing Procedure:
Preparation of Gelling Phase
1. CARBOPOL® 980 was dispersed into purified water containing Disodium EDTA at about 65-70° C. under stirring and kept for about 30-45 min to hydrate for complete swelling.

Preparation of Adapalene Phase
2. Sodium docusate and POLOXAMER™124 were dissolved in glycerin at about 55-60° C.
3. To the above solution Adapalene was dispersed with stirring for about 20 min.

Preparation of Benzoyl Peroxide Phase
4. Propylene glycol was dissolved in purified water and to this mixture Benzoyl peroxide was added with stirring for about 20-25 min.

Preparation of Gel.
5. Adapalene slurry from 3 was added to the gel phase of 1 at about 15-20° C. followed by BPO slurry from 4 with homogenizing for about 30 min.
6. To the dispersion of 5, Isopropyl myristate and Sorbitan oleate were added with homogenization for about 10 min. followed by adjustment of pH with 10% sodium hydroxide solution to pH 4.6.
7. The final volume is adjusted with remaining quantity purified water under stirring.

Example 2

Preparation of an Aqueous Gel Composition Comprising CARBOPOL® 980 as Gelling Agent and Isohexadecane as Penetrating Agent

TABLE 2

| Sr. No. | Ingredients/Components | Qty. in % w/w |
|---|---|---|
| 1 | Adapalene | 0.1 |
| 2 | Benzoyl peroxide | 2.5 |
| 3 | Disodium EDTA | 0.1 |
| 4 | Glycerin | 4.0 |
| 5 | Propylene Glycol | 4.0 |
| 6 | Sodium docusate | 0.05 |
| 7 | POLOXAMER ™ 124 | 0.2 |
| 8 | CARBOPOL ® 980 | 1.1 |
| 9 | Sorbitan oleate | 0.5 |
| 10 | Isohexadecane | 1.0 |
| 11 | Sodium hydroxide | 0.2 |
| 12 | Purified water | 86.25 |

Manufacturing Procedure:
Preparation of Gelling Phase
1. CARBOPOL® 980 was dispersed into purified water containing Disodium EDTA at about 65-70° C. under stirring and kept for about 30-45 min to hydrate for complete swelling.

Preparation of Adapalene Phase
2. Sodium docusate and Poloxamer™124 were dissolved in glycerin at about 55-60° C.
3. To the above solution Adapalene was dispersed with stirring for about 20 min.

Preparation of Benzoyl Peroxide Phase

4. Propylene glycol was dissolved in purified water and to this mixture Benzoyl peroxide was added with stirring for about 20-25 min.

Preparation of Gel

5. Adapalene slurry from 3 was added to the gel phase of 1 at about 15-20° C. followed by BPO slurry from 4 with homogenizing for about 30 min.
6. To the dispersion of 5, isohexadecane and sorbitan oleate were added with homogenization for about 10 min. followed by adjustment of pH with 10% sodium hydroxide solution to pH 4.6.
7. The final volume is adjusted with remaining quantity purified water under stirring.

The gel composition of Example 2 was stored at 40° C./75% relative humidity (RH) for three (3) months. Stability after three months with respect to degradation of benzoyl peroxide to benzoic acid was determined. At the end of three months, it was determined that benzoic acid degradation by-product was no more than about 5%.

Example 3

Preparation of an Aqueous Gel Composition Comprising CARBOPOL® 980 as Gelling Agent and Octyldodecanol as a Penetrating Agent The ingredients for use in this example are set forth below in Table 3.

TABLE 3

| Sr. No. | Ingredients/Components | Qty. in % w/w |
|---|---|---|
| 1 | Adapalene | 0.1 |
| 2 | Benzoyl peroxide | 2.5 |
| 3 | Disodium EDTA | 0.1 |
| 4 | Glycerin | 4.0 |
| 5 | Propylene Glycol | 4.0 |
| 6 | Sodium docusate | 0.05 |
| 7 | POLOXAMER ™ 124 | 0.2 |
| 8 | CARBOPOL ® 980 | 1.1 |
| 9 | Sorbitan oleate | 0.5 |
| 10 | Octyldodecanol | 1.0 |
| 11 | Sodium hydroxide | 0.2 |
| 12 | Purified water | 86.25 |

Manufacturing Procedure:

Preparation of Gelling Phase

1. CARBOPOL® 980 was dispersed into purified water containing Disodium EDTA at about 65-70° C. under stirring and kept for about 30-45 min to hydrate for complete swelling.

Preparation of Adapalene Phase

2. Sodium docusate and Poloxamer™124 were dissolved in glycerin at about 55-60° C.
3. To the above solution Adapalene was dispersed with stirring for about 20 min.

Preparation of Benzoyl Peroxide Phase

4. Propylene glycol was dissolved in purified water and to this mixture Benzoyl peroxide was added with stirring for about 20-25 min.

Preparation of Gel

5. Adapalene slurry from 3 was added to the gel phase of 1 at about 15-20° C. followed by BPO slurry from 4 with homogenizing for about 30 min.
6. To the dispersion of 5, octyldodecanol and sorbitan oleate were added with homogenization for about 10 min. followed by adjustment of pH with 10% sodium hydroxide solution to pH 4.6.
7. The final volume is adjusted with remaining quantity purified water under stirring.

Example 4

Preparation of an Aqueous Gel Composition Comprising CARBOPOL® 980 as Gelling Agent and Octyldodecanol as a Penetrating Agent without Sorbitan Oleate The ingredients for use in this example are set forth below in Table 4.

TABLE 4

| Sr. No. | Ingredients/Components | Qty. in % w/w |
|---|---|---|
| 1 | Adapalene | 0.1 |
| 2 | Benzoyl peroxide | 2.5 |
| 3 | Disodium EDTA | 0.1 |
| 4 | Glycerin | 4.0 |
| 5 | Propylene Glycol | 4.0 |
| 6 | Sodium docusate | 0.05 |
| 7 | POLOXAMER ™ 124 | 0.2 |
| 8 | CARBOPOL ® 980 | 1.1 |
| 9 | Octyldodecanol | 1.0 |
| 10 | Sodium hydroxide | 0.2 |
| 11 | Purified water | 86.75 |

Manufacturing Procedure:

Preparation of Gelling Phase

1. CARBOPOL®980 was dispersed into purified water containing Disodium EDTA at about 65-70° C. under stirring and kept for about 30-45 min to hydrate for complete swelling.

Preparation of Adapalene Phase

2. Sodium decussate and POLOXAMER™124 were dissolved in glycerin at about 55-60° C.
3. To the above solution Adapalene was dispersed with stirring for about 20 min.

Preparation of Benzoyl Peroxide Phase

4. Propylene glycol was dissolved in purified water and to this mixture Benzoyl peroxide was added with stirring for about 20-25 min.

Preparation of Gel

5. Adapalene slurry from 3 was added to the gel phase of 1 at about 15-20° C. followed by BPO slurry from 4 with homogenizing for about 30 min.
6. To the dispersion of 5, octyldodecanol was added with homogenization for about 10 min. followed by adjustment of pH with 10% sodium hydroxide solution to pH 4.6.
7. The final volume is adjusted with remaining quantity purified water under stirring.

Example 5

Preparation of an Aqueous Gel Composition Comprising CARBOPOL® 980 as Gelling Agent and Medium Chain Triglyceride as a Penetrating Agent and without Sorbitan Oleate The ingredients for use in this example are set forth below in Table 5.

TABLE 5

| Sr. No. | Ingredients/Components | Qty. in % w/w |
|---|---|---|
| 1 | Adapalene | 0.1 |
| 2 | Benzoyl peroxide | 2.5 |
| 3 | Disodium EDTA | 0.1 |
| 4 | Glycerin | 4 |
| 5 | Propylene Glycol | 4 |
| 6 | Sodium docusate | 0.05 |
| 7 | POLOXAMER ™ 124 | 0.2 |
| 8 | CARBOPOL ® 980 | 1.1 |
| 9 | Medium Chain Triglyceride | 1 |
| 10 | sodium hydroxide | 0.2 |
| 11 | Purified water | 86.75 |

Manufacturing Procedure:
Preparation of Gelling Phase
1. CARBOPOL®980 was dispersed into purified water containing Disodium EDTA at about 65-70° C. under stirring and kept for about 30-45 min to hydrate for complete swelling.

Preparation of Adapalene Phase
2. Sodium docusate and POLOXAMER™124 were dissolved in glycerin at about 55-60° C.
3. To the above solution Adapalene was dispersed with stirring for about 20 min.

Preparation of Benzoyl Peroxide Phase
4. Propylene glycol was dissolved in purified water and to this mixture Benzoyl peroxide was added with stirring for about 20-25 min.

Preparation of Gel
5. Adapalene slurry from 3 was added to the gel phase of 1 at about 15-20° C. followed by BPO slurry from 4 with homogenizing for about 30 min.
6. To the dispersion of 5, Medium Chain Triglyceride was added with homogenization for about 10 min. followed by adjustment of pH with 10% sodium hydroxide solution to pH 4.6.
7. The final volume is adjusted with remaining quantity purified water under stirring.

Example 6

Preparation of an Aqueous Gel Composition Comprising CARBOPOL® 980 as Gelling Agent and Cyclomethicone as a Penetrating Agent without Sorbitan Oleate The ingredients for use in this example are set forth below in Table 6.

TABLE 6

| Sr. No. | Ingredients/Components | Qty. in % w/w |
|---|---|---|
| 1 | Adapalene | 0.1 |
| 2 | Benzoyl peroxide | 2.5 |
| 3 | Disodium EDTA | 0.1 |
| 4 | Glycerin | 4 |
| 5 | Propylene Glycol | 4 |
| 6 | Sodium docusate | 0.05 |
| 7 | Poloxamer ™ 124 | 0.2 |
| 8 | CARBOPOL ® 980 | 1.1 |
| 9 | Cyclomethicone | 1 |
| 10 | sodium hydroxide | 0.2 |
| 11 | Purified water | 86.25 |

Manufacturing Procedure:
Preparation of Gelling Phase
1. CARBOPOL®980 was dispersed into purified water containing Disodium EDTA at about 65-70° C. under stirring and kept for about 30-45 min to hydrate for complete swelling.

Preparation of Adapalene Phase
2. Sodium docusate and POLOXAMER™124 were dissolved in glycerin at about 55-60° C.
3. To the above solution Adapalene was dispersed with stirring for about 20 min.

Preparation of Benzoyl Peroxide Phase
4. Propylene glycol was dissolved in purified water and to this mixture Benzoyl peroxide was added with stirring for about 20-25 min.

Preparation of Gel
5. Adapalene slurry from 3 was added to the gel phase of 1 at about 15-20° C. followed by BPO slurry from 4 with homogenizing for about 30 min.
6. To the dispersion of 5, cyclomethicone was added with homogenization for about 10 min. followed by adjustment of pH with 10% sodium hydroxide solution to pH 4.6.
7. The final volume is adjusted with remaining quantity purified water under stirring.

Example 7

Preparation of an Aqueous Gel Composition Comprising CARBOPOL® 980 as Gelling Agent and Cyclomethicone as a Penetrating Agent The ingredients for use in this example are set forth below in Table 7

TABLE 7

| Sr. No. | Ingredients/Components | Qty. in % w/w |
|---|---|---|
| 1 | Adapalene | 0.1 |
| 2 | Benzoyl peroxide | 2.5 |
| 3 | Disodium EDTA | 0.1 |
| 4 | Glycerin | 5 |
| 5 | Propylene Glycol | 10 |
| 6 | Sodium docusate | 0.3 |
| 7 | POLOXAMER ™ 124 | 0.2 |
| 8 | CARBOPOL ® 980 | 1.1 |
| 9 | Cyclomethicone | 1 |
| 10 | Sorbitan oleate | 1 |
| 11 | Sodium hydroxide | 0.2 |
| 12 | Purified water | Qs to 100 |

Manufacturing Procedure:
Preparation of Gelling Phase
1. CARBOPOL®980 was dispersed into purified water containing Disodium EDTA and Sorbian oleate at about 65-70° C. under stirring and kept for about 30-45 min to hydrate for complete swelling.

Preparation of Adapalene Phase
2. Sodium docusate and POLOXAMER™124 were dissolved in glycerin at about 55-60° C.
3. To the above solution Adapalene was dispersed with stifling for about 20 min.

Preparation of Benzoyl Peroxide Phase
4. Propylene glycol was dissolved in purified water and to this mixture Benzoyl peroxide was added with stifling for about 20-25 min.

Preparation of Gel

5. Adapalene slurry from 3 was added to the gel phase of 1 at about 15-20° C. followed by BPO slurry from 4 with homogenizing for about 30 min.
6. To the dispersion of 5, cyclomethicone was added with homogenization for about 10 min. followed by adjustment of pH with 10% sodium hydroxide solution to pH 4.6.
7. The final volume is adjusted with remaining quantity of purified water under stifling.

Example 8

Preparation of an Aqueous Gel Composition Comprising PEMULEN™TR1 as Gelling Agent and Octyldodecanol as a Penetrating Agent The ingredients for use in this example are set forth below in Table 8

TABLE 8

| Sr. No. | Ingredients/Components | Qty. in % w/w |
|---|---|---|
| 1 | Adapalene | 0.1 |
| 2 | Benzoyl peroxide | 2.5 |
| 3 | PEMULEN ™ TR 1 | 1.2 |
| 4 | Silicon dioxide (RxCIPIENTS ® GL200) | 0.25 |
| 5 | Disodium EDTA | 0.1 |
| 6 | Glycerin | 5.0 |
| 7 | Propylene Glycol | 10.0 |
| 8 | Sodium Docusate | 0.3 |
| 9 | POLOXAMER ™ 124 | 0.2 |
| 10 | Sorbitan oleate | 1.0 |
| 11 | Octyldodecanol | 1.0 |
| 12 | Sodium hydroxide | 0.1 |
| 13 | Purified water | Qs to 100 |

Manufacturing Procedure:
Preparation of Gelling Phase
1. PEMULEN™TR and silicon dioxide were added slowly under stirring into purified water containing Disodium EDTA and Docusate sodium at about 65-70° C. and kept for about 30-45 min to hydrate for complete swelling. To this, octyldodecanol, glycerine and sorbitan oleate were added under stirring.
Preparation of Adapalene Phase
2. POLOXAMER™124 was dissolved in propylene glycol at about 55-60° C.
3. To the above solution, adapalene was dispersed with stifling for about 20 min.
Preparation of Benzoyl Peroxide Phase
4. Propylene glycol was dissolved in purified water and to this mixture BPO was added with stifling for about 20-25 min.
Preparation of Gel
5. Adapalene slurry from step 3 was added to the gel phase of 1 at about 15-20° C. followed by BPO slurry from 4 with homogenizing for about 30 min.
6. The dispersion of 5, adjusted to pH 5 with 5% sodium hydroxide solution.
7. The final volume is adjusted with remaining quantity of purified water under stirring.

Example 9

Preparation of an Aqueous Gel Composition Comprising CARBOPOL® 980 and PEMULEN™TR-1 as Gelling Agent and Cyclomethicone as a Penetrating Agent The ingredients for use in this example are set forth below in Table 9

TABLE 9

| Sr. No. | Ingredients/Components | Qty. in % w/w |
|---|---|---|
| 1 | Adapalene | 0.1 |
| 2 | Hydrous Benzoyl Peroxide | 2.5 |
| 3 | Edetate Disodium | 0.1 |
| 4 | Docusate sodium | 0.3 |
| 5 | Glycerin (Glycerol Anhydrous) | 5.0 |
| 6 | Propylene glycol | 10.0 |
| 7 | POLOXAMER ™ 124 | 0.2 |
| 8 | CARBOPOL ® 980 | 0.7 |
| 9 | PEMULEN ™ TR-1 | 0.3 |
| 10 | Sorbitan oleate (MONTANE ™ 80 PHA premium) | 1.0 |
| 11 | Cyclomethicone | 1.0 |
| 12 | Sodium hydroxide | 0.2 |
| 13 | Purified water | Qs to 100 |

Manufacturing Procedure:
Preparation of Gelling Phase
1. PEMULEN™TR and CARBOPOL® 980 were added slowly under stirring into purified water containing Disodium EDTA and Docusate sodium at about 65-70° C. and kept for about 30-45 min. to hydrate for complete swelling. To this cyclomethicone, glycerin and Sorbitan oleate were added under stirring.
Preparation of Adapalene Phase
2. POLOXAMER™124 was dissolved in propylene glycol at about 55-60° C.
3. To the above solution Adapalene was dispersed with stirring for about 20 min.
Preparation of Benzoyl Peroxide Phase
4. Propylene glycol was dissolved in purified water and to this mixture BPO was added with stifling for about 20-25 min.
Preparation of Gel
5. Adapalene slurry from 3 was added to the gel phase of 1 at about 15-20° C. followed by BPO slurry from 4 with homogenizing for about 30 min.
6. The dispersion of 5, adjusted to pH 5 with 5% sodium hydroxide solution.
7. The final volume is adjusted with remaining quantity purified water under stirring.

The gel composition of Example 9 was stored at 40° C./75% RH for one (1) month. The stability after one month with respect to degradation of benzoyl peroxide to benzoic acid was determined. At the end of one month, it was determined that benzoic acid degradation by-product was no more than about 2%.

We claim:
1. An aqueous gel for the treatment of acne comprising 0.1% adapalene and 2.5% benzoyl peroxide, as active ingredients, 0.1% disodium EDTA, 4.0% glycerin, 4.0% propylene glycol, 0.05% sodium docusate, 0.2% polyoxyethylenated/polyoxypropylenated copolymers, 1.1% carbomer homopolymer, 0.5% sorbitan oleate and 1% cyclomethicone in purified water; wherein both the active ingredients are stabilized in hydrophilic gelling matrix of pH dependent gelling agent.

2. The aqueous gel of claim 1, wherein the carbomer homopolymer is acrylic acid crosslinked with allyl sucrose or allylpentaerythritol.

3. An aqueous gel for the treatment of acne comprising 0.1% adapalene and 2.5% benzoyl peroxide, as active ingredients, 0.1% disodium EDTA, 5.0% glycerin, 10.0% propylene glycol, 0.3% sodium docusate, 0.2% polyoxyethylenated/polyoxypropylenated copolymers, 0.7% carbomer homopolymer, 0.3% carbomer copolymer, 1.0% sorbitan oleate and 1.0% cyclomethicone in purified water; wherein both the active ingredients are stabilized in hydrophilic gelling matrix of pH dependent gelling agent.

4. The aqueous gel of claim 3, wherein the carbomer homopolymer is acrylic acid crosslinked with allyl sucrose or allylpentaerythritol; and the carbomer copolymer is acrylate/C10-C30-alkylacrylate copolymer.

* * * * *